United States Patent [19]
Gadberry et al.

[11] Patent Number: 5,217,114
[45] Date of Patent: Jun. 8, 1993

[54] CATHETER PACKAGE

[75] Inventors: Donald L. Gadberry, Huntington Beach; Vincent C. Tangherlini, Rancho Santa Margarita; Robert P. Cooper, Yorba Linda, all of Calif.

[73] Assignee: Applied Vascular Devices, Inc., Laguna Hills, Calif.

[21] Appl. No.: 701,435

[22] Filed: May 15, 1991

[51] Int. Cl.⁵ .............................................. B65D 85/20
[52] U.S. Cl. .................................. 206/364; 53/492; 206/439; 220/300
[58] Field of Search .............. 53/492; 206/361-370, 206/438, 439; 215/330-332, 246, 352; 220/293, 300, 302; 604/192, 197, 198, 263

[56] References Cited

U.S. PATENT DOCUMENTS

| | | | |
|---|---|---|---|
| 1,216,869 | 2/1917 | Snigo | 220/300 |
| 2,954,139 | 9/1960 | Owens | 215/246 |
| 2,997,043 | 8/1961 | Flynn . | |
| 3,149,717 | 9/1964 | Castelli | 206/365 |
| 3,203,545 | 8/1965 | Grossman | 206/364 |
| 3,235,069 | 2/1966 | Bennett et al. | 206/364 |
| 3,333,682 | 8/1967 | Burke | 206/365 |
| 3,606,001 | 9/1971 | Talonn . | |
| 3,783,996 | 1/1974 | Gerard et al. | 206/364 |
| 3,794,042 | 2/1974 | Deklotz et al. | 206/364 |
| 3,968,876 | 7/1976 | Brookfield | 206/365 |
| 4,018,640 | 4/1977 | Amberg | 215/246 |
| 4,020,948 | 5/1977 | Won | 215/352 |
| 4,453,936 | 6/1984 | Cassou . | |
| 4,500,312 | 2/1985 | McFarlane . | |
| 4,573,981 | 3/1986 | McFarlane . | |

FOREIGN PATENT DOCUMENTS

0513212 2/1921 France ................ 206/365

Primary Examiner—Jimmy G. Foster
Attorney, Agent, or Firm—Richard L. Myers

[57] ABSTRACT

A package for a catheter having a proximal end and a distal end, includes a tube defining a cavity along an elongate axis, the cavity being configured to receive at least the distal end of the catheter. Access means includes a housing fixed to the proximal end of the tube and a cap rotatable to engage the housing in a first position to seal the cavity, and to disengage the housing in a second position to provide access to the cavity. A circumferential tear-strip is configured and disposed to provide a high degree of control over the separation of the housing and cap. An O-ring, which forms a seal between the cap and housing, is disposed relative to a circumferential shoulder which cooperates with a camming surface to cause the cap to pop from the housing when rotated. An associated method includes the steps of rotating the cap a first angular distance to engage the camming surface and a second angular distance to cause the O-ring to traverse the shoulder.

26 Claims, 3 Drawing Sheets

CATHETER PACKAGE

BACKGROUND OF THE INVENTION

1. Field of the Invention

This invention relates generally to packages for catheters and more specifically to elongate packages which maintain the catheter in a straight, non-spiral configuration.

2. Discussion of the Prior Art

A catheter is a device which is typically inserted through the skin of a patient and introduced into a body cavity, such as the heart, or a body passage such as a blood vessel. In these locations the catheter can be used to introduce or withdraw fluids, measure pressures, provide for visualization, and perform other mechanical and electrical functions. A catheter typically consists of an elongate cannula and a hub which facilitates attachment of the cannula to various external apparatus such as monitors.

Catheters are usually packaged in sterile containers which differ primarily in the configuration of the catheter within the package. Some packages maintain the catheter in a spiral configuration while other packages maintain the catheter in a straight, elongate configuration.

The elongate catheter packages consist generally of a long tube which receives the cannula of the catheter and an access device which receives the hub of the catheter. The access device typically includes a housing and a cap which is removable to provide access to the catheter in the tube. It is the interrelationship of the cap and the housing of the access device which is of particular interest to this invention.

In the past, caps have been slidably mounted on the housings and held in place by heat-shrink tubing which extends over the intersection of the cap and the housing. This tubing has been provided with an axial tear-strip which is removable to permit the cap to be withdrawn axially from the housing. In the absence of any seal between the cap and housing, a tight fit between the cap and the housing has been relied upon to help maintain the sterility of the packaged catheter. This requirement for a tight fit has made it very difficult to remove the cap so that it has often been necessary to grasp each of the cap and the housing with the entire hand in order to accommodate the required forces for removal.

Sterility has been a problem for several reasons. With the packages of the past, once the tear-strip was removed, if the catheter was not used, it nevertheless had to be discarded because it could not be resterilized. Furthermore, the indelicate grasping of the housing and cap often meant that non-sterile hands compromised sterile regions of the package and, more importantly, the sterile catheter.

Catheter packages are typically opened by a nurse who is not part of the sterile environment. While it is the job of that nurse to open the catheter package, only someone in the sterile environment should touch the catheter. This has presented a problem with respect to catheter packages of the past wherein the catheter hub has been deeply seated in the housing. In order for the catheter to be removed from the housing sufficiently that someone in the sterile environment can grasp and remove the catheter from the package, the nurse opening the package has typically attempted to shake the catheter package downwardly until the hub of the catheter clears the housing. Since the hub accounts for a large percentage of the weight of the catheter, the shaking of the package must be done carefully to prevent the entire catheter from falling on the floor.

Certainly the opening of a catheter package is not the most important procedure occurring in an operating room. Structures which have required rough and indelicate procedures to provide access to a sterile catheter simply cannot be tolerated in this stressful environment.

SUMMARY OF THE INVENTION

These problems associated with the prior art have been overcome with the present invention which includes a seal between the cap and the housing and provides for the simple, delicate opening of a catheter package with a high degree of tactile feedback and control. The seal not only facilitates initial sterilization of the package, but also accommodates resterilization if required. Since the invention does not rely on heat-shrink properties for sterilization, a tear-strip can be engineered for other purposes such as contributing to the ergonomics associated with opening the package.

Both the housing and the cap can be provided with wings which are easily engagable by fingers of the user in order to remove the cap. These elements can also be configured to provide a screw fitting between the cap and housing or preferably a bayonet fitting which requires less than a quarter turn to release the cap from the housing.

In a preferred embodiment, the tear-strip is disposed over the intersection of the cap and housing and is provided with a line of perforations having a density that is controllable to provide the desired tactile feel for opening. The quarter turn required by the bayonet fitting cracks this strip along the perforations to permit removal of the cap. Once the strip is separated, its two portions remain with the respective cap and housing. These portions can be coded, for example with the same color, in order to facilitate reattachment of the associated cap and housing.

The cap and housing are sized so that at least a portion of the hub of the catheter extends from the housing and is easily engagable by a person in the sterile environment once the cap is removed. The user will greatly appreciate the elements forming the seal and the bayonet fitting, which combine to cause the cap to jump axially from the housing during the quarter turn.

Thus the invention provides a catheter package which accommodates sterilization, provides for a strong attachment between the cap and housing, but permits a simple delicate removal of the cap to obtain access to the sterile catheter.

These and other features and advantages of the invention will be more apparent with a description of preferred embodiments and reference to the associated drawings.

DESCRIPTION OF PREFERRED EMBODIMENTS

Figure 1:
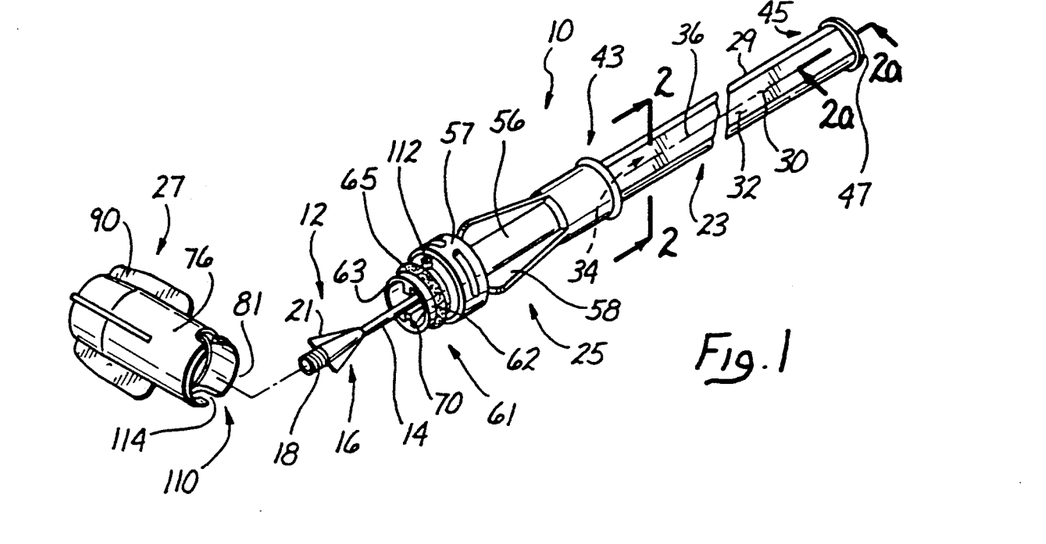
FIG. 1 is a perspective view of a catheter having a cannula and a hub, and a catheter package including a housing and cap in accordance with the present invention.

A catheter package is illustrated in FIG. 1 and designated generally by the reference number 10. It is the purpose of the package 10 to enclose, transport and provide storage for a catheter 12 which is usually in a sterilized condition. The catheter includes a cannula 14 and a hub 116. The cannula 14 is typically very narrow and long facilitating its insertion into body cavities, such as the heart, and body conduits, such as blood vessels. While the cannula 14 associated with catheters may differ as to the number of lumens in the cannula it will generally have a very smooth outer surface which is cylindrical in shape facilitating insertion into the body of a patient.

In comparison, the hub 16 associated with the catheter 12 will vary significantly depending on the intended use of the catheter 112. In the illustrated embodiment, the hub 16 includes a Luer fitting 18 and a pair of extensions 21 which are disposed between the fitting 18 and the cannula 14.

This catheter 12 is adapted for insertion into the package 10 which is composed of an elongate tube 23, and an access device including a housing 25 and a cap 27. The tube 23 has an elongate o configuration suitable for packaging the catheter 12 with the cannula 14 in a straight, unbent configuration. For example, the tube 23 may vary in length of about thirty inches with an outer diameter of about and one-half inch.

Figure 2:
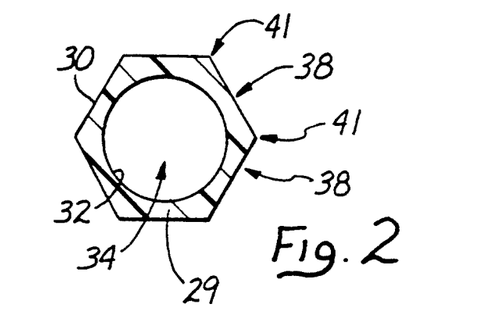
FIG. 2 is a radial cross-section view of the catheter package taken along lines 2—2 of FIG. 1.

The tube 23 is characterized by walls 29 which have an outer surface 30, and an inner surface 32 which defines a longitudinal cavity 34 along a central axis 36. It is of particular advantage to this embodiment that the outer surface 30 of the walls 29 are be non-circular in cross-section so that the tube 23 does not tend to roll when placed on a flat surface. In a preferred embodiment, the outer surface 30 may have the configuration of a polygon, such as a hexagon, as illustrated in FIG. 2.

If the outer surface 30 is provided with a polygonal cross-section, it may be desirable that the inner surface 32 be provided with a circular cross-section. These shapes will provide the walls 29 with relatively thin sections 38 which alternate with relatively thick sections 41 around the circumference of the tube 23. With this configuration of the tube 23, the relatively thick sections 41 function as axial ribs greatly increasing the rigidity of the tube 23 which protects the cannula 14 of the catheter 12.

Figure 2A:
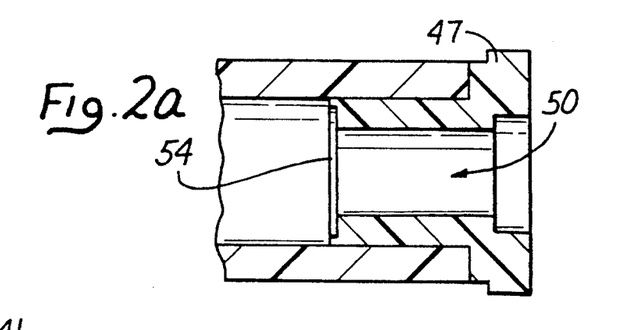
FIG. 2a is an axial cross-section view of the catheter package taken along lines 2a–2a of FIG. 1.

The tube 23 extends from a proximal end 43 to a distal end 45, where a plug 47 can be provided to seal the cavity 34. The plug 47 can be glued to the distal end 45 of the tube 23 and provided with an axial bore 50 which extends into the cavity 34. The surface of the plug 47 facing the cavity 34 can be provided with an axial recess 52 which is adapted to receive and protect a sheet of material 54 formed from TYVEK ®, a trademark of DuPont de Nemours Company. The TYVEK ® material is particularly helpful to the sterilization of the package 10 in that it permits the transmission of sterilization gasses while inhibiting the passage of any microbial contaminants.

At the proximal end 43 of the tube 23, the housing 25 and removable cap 27 provide means for accessing the catheter 12 in the cavity 34. In this embodiment, the housing 25, which can be glued or otherwise fixed to the tube 23 includes a relatively small cylindrical section 56 and an enlarged cylindrical section 57. A pair of wings 58 extend from the relatively small section 56 radially outwardly and provide means for gripping the housing 25 using only the fingers of the person opening the package. The housing 25 also includes a projection 61 which extends from the enlarged section 57 and is configured to mate with the cap 27 to seal the catheter package 10.

In the illustrated embodiment, the projection 61 has a generally cylindrical outer surface 62 which extends to a radial end surface 63. The outer surface 62 is provided with a circumferential recess 64 shaped to receive an 0-ring 65. Both the cylindrical sections 56, 57 and the projection 61 define an interior bore 67 which is axially aligned with and extends into the cavity 34 of the tube 23.

A pair of opposing splines 70 are provided on the projection 61 and extend into the bore 67. These splines 70 provide means for inhibiting rotation of the catheter 12 when the extensions 21 extend partially into the bore 67. This can be important since during transportation vibration tend to cause the catheter 12 to rotate within the package 10 creating unnecessary wear on the catheter 12.

It is of particular advantage that the bore 67 in the housing 25 be of a diameter less than the width of the extensions 21 of the catheter 12. This will insure that less than all of the hub 16 extends into the bore 67. Then, when the cap 27 is removed, the catheter 12 projects slightly from the housing 25 permitting any person in the sterile field to grasp the hub 18 and remove the catheter 12 from the package 10.

Between the cylindrical section 56 and the projection 61, the enlarged section 57 is provided with two surfaces which are of particular interest to the present invention. The first is a surface 72 which is cylindrical and extends axially of the package 10. The second is a surface 74 which is planar extends radially of the projection 61.

The cap 27 is formed with walls 76 which define a central cavity 78 having a diameter greater than that of the projection 61 associated with the housing, 25. The radius of the cavity 78 should be sufficiently large to accommodate the largest radial dimension of the hub 16, such as the radial dimension of the extensions 21 associated with the hub 16.

Figure 6:
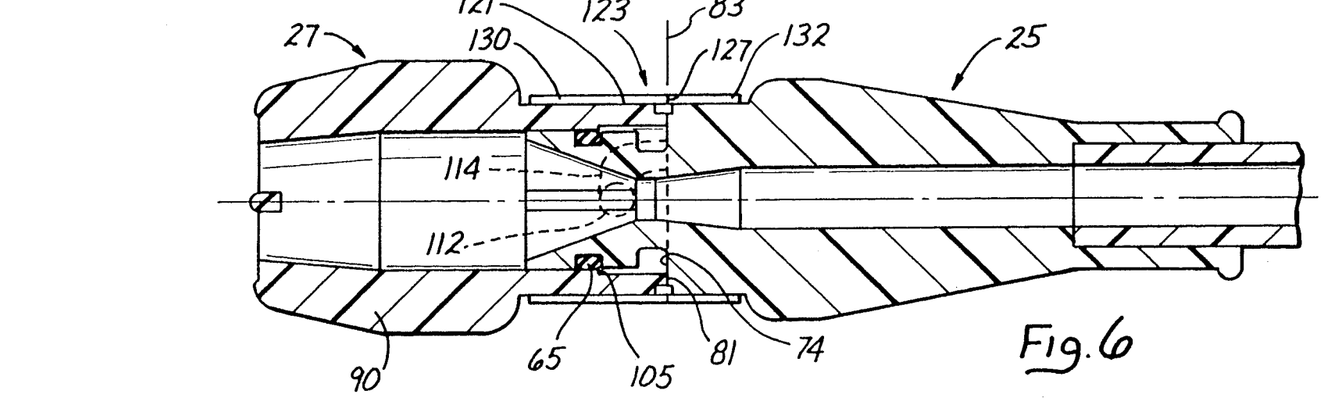
FIG. 6 is an axial cross-section view of the catheter package of FIG. 1 illustrating the cap attached to the housing and secured by a circumferential tear-strip.

The walls 76 extend distally to a radial surface 81 which abuts the surface 74 when the cap 27 is fixed to the housing 25, as illustrated in FIG. 6. In this position, the radial surface 81 of the cap 27 and the radial surface 74 of the housing 25 define a plane of separation which is designated by the reference numeral 83 in FIG. 6.

At the opposite end of the cap 27, the cavity 78 is sealed by a second sheet of TYVEK ® material 85.

Having this TYVEK® material at both ends of the package 10 greatly facilitates sterilization of the catheter 12 and outgassing of the package 10.

Extending radially from the walls 76 of the cap 27 are a plurality of wings 90 which, in a preferred embodiment, are equal in number and spacing to the wings 58 associated with the housing 25. These wings 90 may extend from the walls 76 a distance such as 3/16" in order to provide suitable leverage and friction to accommodate gripping the cap 27, for example between the fingers of one hand. With the wings 58 of the housing 25 performing a similar function for the opposite hand, it is quite easy to delicately engage the extensions 21 and 90 and rotate the cap 27 to permit separation of the cap 27 and housing 25.

In a particular embodiment it may be desirable to enlarge the cap 27 and housing 25 sufficiently to accommodate a catheter 12 having an enlarged hub 16 such as a stop-cock (not shown). In such an embodiment the walls 76 of the cap 27 might have a considerable diameter so that it would be desirable to limit the projection of the wings 90. In this case, it might be desirable to provide other means for enhancing the users grip on the cap 87, such as providing a knurled outer surface on the walls 76.

As best illustrated in FIG. 2, the cap 27 is configured so that the inner surface of the walls 76 include a clearance surface 101 and an engagement surface 103. The clearance surface 101 is disposed adjacent the radial surface 81 and is provided with a relatively large diameter sufficient to clear the 0-ring 65 when the projection 61 is inserted into the cap 27. The engagement surface 103 is slightly smaller in diameter and tends to compress the 0-ring 65 to form a seal between the cap 27 and housing 25. A shoulder 105 extends radially between the two surfaces 101 and 103.

Certainly a primary purpose associated with the housing 25 and the cap 27 is to maintain the catheter 12 in the package 10 until its use is required. Of course it is desirable that the cap 27 also be removable from the housing 25 in order to gain access to the catheter 12.

This removable attachment of the cap 27 to the housing 25 can be accomplished in several manners. The prior art has relied upon sliding the cap axially across a detent. This may provide for a particularly secure fit and is not always easy to accomplish. A preferred motion for separation is a rotation motion which is provide in accordance with the present invention. A screw thread (not shown) could be relied on to rotatably release the cap 27, but in the illustrated embodiment a bayonet fitting shown generally at 110 is provided.

This bayonet fitting 110 will typically include a pin 112 on one of the mating parts, such as the housing 25, and a groove 114 on the other of the mating parts, such as the cap 27. The groove 114 is defined in part by a camming surface 115 which extends between an axial portion 116 and a radial portion 118 of the groove 114. When the cap 27 is initially mounted, the pin is received in the axial portion 116 and then the cap 27 is rotated as the pin 112 moves along the radial portion 118 of the groove 114.

It will be apparent that in this configuration, the attaching means, including the pin 112 and the groove 114, is disposed between the surface 63 which terminates the projection 61 and the surface 81 which terminates the cap 27. In such an embodiment the seal means, such as the 0-ring 65, is disposed between the surfaces 63 and 81 on the side of the bayonet fitting 110 opposite the surface 81.

The angular length of the radial portion 118 of the groove 114 determines the amount of angular displacement required to lock the cap 27 to the housing 25, or in the alternative, to remove the cap 27 from the housing 25. In a preferred embodiment a quarter turn, or about 90°, is most desirable.

When the cap 27 is attached to the housing 25, the surface 81 associated with the cap abuts the surface 74 associated with the enlarged section 57. The pin 112 is received in the radial portion 118 of the groove 114 and the O-ring 65 is compressed between the projection 61 and the engagement surface 103. This relationship is illustrated in FIG. 6 which also shows a continuous cylindrical surface which is formed by the outer surface of the walls 76 and the outer surface 72 of the enlarged cylindrical section 57. This surface, collectively designated by the reference numeral 121 in FIG. 6, is disposed between and protected by the wings 58 and 90 associated with the housing 25 and cap 27, respectively.

The surface 121 is also divided by the plane of separation 83. These characteristics make the surface 121 particularly adapted to receive a circumferential tear-strip 123 having a line of perforations 127 which divides the strip into a cap portion 130 and a housing portion 132.

In order to provide the desired tactile feeling in opening the catheter package 10, it is desirable that a relatively large initial force be required to start the cap 27 into rotation, but that relatively minor forces be required to thereafter remove the cap 27 from the housing 25. While it might be apparent that a detent could be provided at the end of the groove 114, this may not provide sufficient design parameters to control the exact feeling desired.

Thus, in a preferred embodiment, the tear-strip 123 is adhered to the surface 121 across the plane of separation 83. With the line of perforations 127 disposed in the plane 83, the initial forces rotating the cap 27 relative to the housing 25 tends to separate the strip 123 into the cap portion 130 and the housing portion 132. This tendency to separate occurs along the line of perforations 127 with the housing portion 127 rotating in an exactly opposite direction relative to the cap portion 128.

The amount of force required to crack the tear-strip 123 along the line of perforations 127 is dependent upon the material of the tear-strip 123, its thickness, the number of perforations in the line 125, and the length of the strip 123. Each of these parameters provides a designer with characteristics which can be varied to generate exactly the tactile feedback and entry forces desired for a particular access device.

With respect to the material of the tear-strip 123, generally any sheet material is suitable if it has a yield point which will result in breaking rather than stretching in response to a load. In a particular embodiment, paper might be used for the tear-strip 123. On the other hand plastics, such as destructible vinyl, may produce fewer free fibers upon breaking. In a preferred embodiment, the selected material includes Mylar®, a registered trademark of E. I. DuPont de Nemours.

The thickness of the tear-strip 123 can vary between one and five millimeters. A very thin strip may be difficult to handle while a very thick strip tends to produce undesirable bumps at any point of overlap. In a preferred embodiment, the tear-strip 123 has a thickness of 0.002 inches.

The length of the tear-strip 123 and the number of perforations per inch in the line 127, vary inversely in accordance with the desired separation torque. As the length of the strip increases, the separation force increases; but as the number of perforations increase, the separation force decreases. It has been found that the tear-strip 123 functioned best when the perforations are in a range between four and twenty perforations per inch. In one preferred embodiment, the tear-strip 123 has a length of 4.36 inches and eight perforations per inch. In another embodiment, the tear-strip 123 has a length of 2.36 inches and seventeen perforations per inch.

Variations in these four parameters can provide separation torques in a range between 15 and 75 inch-pounds. In the preferred embodiments, separation torques of 55 inch pounds were found to provide reliable sealing and good tactile feedback for opening the package 10.

When the tear-strip 123 is separated along the line 125, the pin 112 is free to move through the groove 114 to permit radial and then axial separation of the cap 27 and housing 25. In a preferred embodiment this separation is carefully controlled in order to provide opening characteristics whereby the cap 27 tends to quickly jump off of the projection 61 in the nature of a snap fitting.

This preferred movement is achieved by the camming surface 121 which guides the pin 112 into a smooth transition from the angular displacement to the axial displacement of the cap 27. While the pin 112 is in contact with this camming surface, the cap 27 begins its axial separation and the O-ring 65 moves over the radial shoulder 105. As the 0-ring 65 on the housing 25 expands from its compressed state, it presses against the shoulder 105 on the cap 27 adding energy to the forces which separates these two elements. These forces continue until the 0-ring 65 is totally clear of the shoulder 105 in the region of the cavity 78 defined by the clearance surface 101 From this point there are only minimal friction forces which resist final removal of the cap 27 from the housing 25. In an embodiment which minimizes the axial length of the cap 27, the 0-ring 65 is disposed immediately adjacent the pin 112, and the shoulder 105 is disposed immediately adjacent the groove 114.

Figure 3:
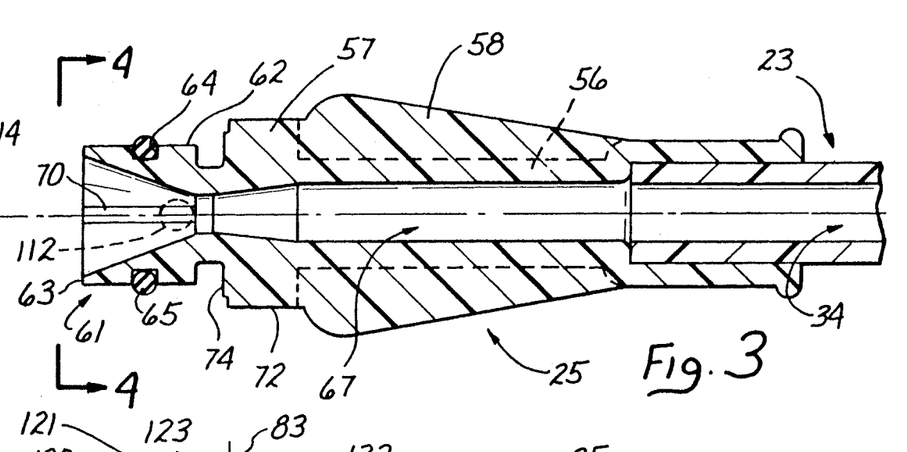
FIG. 3 is a axial cross-section view of the catheter package of FIG. 1 illustrating the cap separating from the housing after the package is opened.
Figure 4:
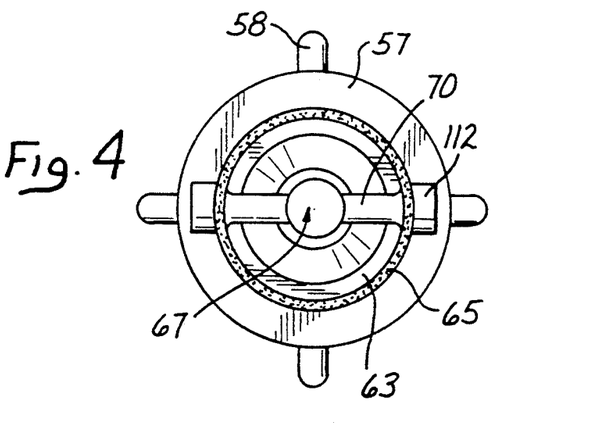
FIG. 4 is an end view of the housing taken along lines 4—4 of FIG. 3.
Figure 5:
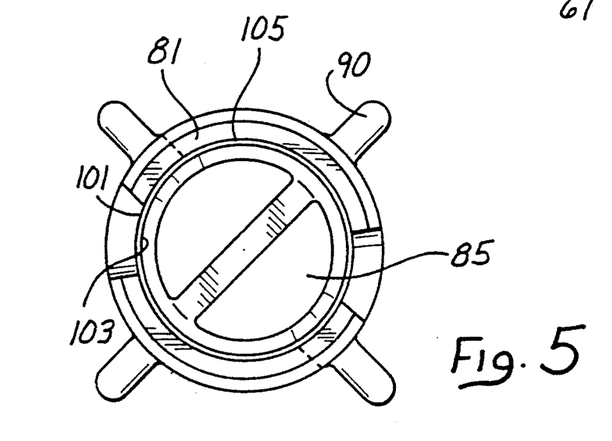
FIG. 5 is an end view of the cap taken along lines 5—5 of FIG. 3.

It will be apparent that these features and advantages can be achieved with other embodiments which basically provide for the switching of various parts and functions. By way of comparison, it will be noted that the embodiment of FIG. 3 includes the 0-ring 65 and pin 112 are associated with the projection 61, while the groove 114 and engagement surface 103 are associated with the cap 27. In the embodiment illustrated in FIG. 6, an O-ring 65a is provided interiorly of the cap 27 and registers with an engagement surface 105a which is disposed on the projection 61.

Figures 7, 8:
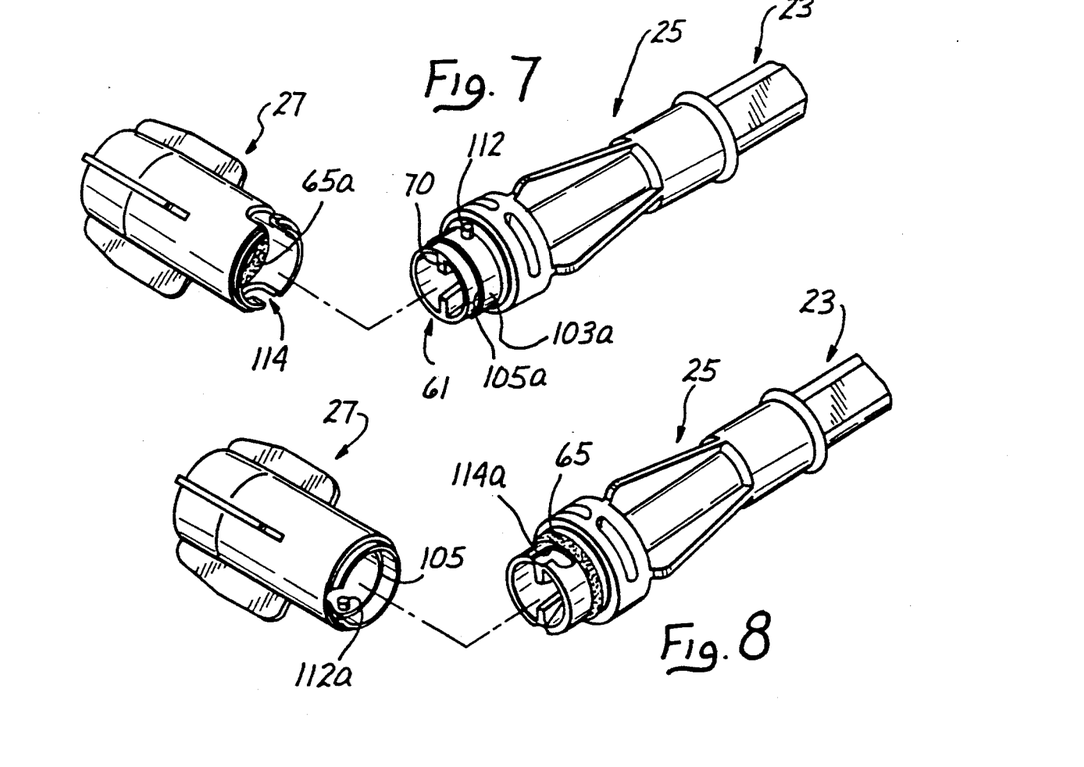
FIG. 7 is a perspective view of an additional embodiment of the catheter package of the present invention.
FIG. 8 is a perspective view of a further embodiment of the catheter package of the present invention.

The embodiment of FIG. 7 differs from the embodiment of FIG. 2 in that a pin 112a is provided in the cap 27 while a mating groove 114a is provided on the projection 61. In all of these embodiments, the preferred bayonet fitting 110 is provided for releasably attaching the cap 27 to the housing 25. Similarly, an O-ring 65a functions to form a seal between the cap 27 and housing 25.

In a preferred embodiment, the tube 23, housing 25, and cap 27 are molded from polycarbonate. The tube 23 is generally opaque while the housing 25 and cap 27 are transparent. The 0-ring 65 is conventionally formed from silicone. All of these materials can be obtained in a medical grade which facilitates sterilization by conventional processes employing ethylene oxide or radiation.

In a preferred method associated with the invention, the cap 27 is rotatable a first angular distance, such as sixty degrees, relative to the housing 25 to provide for the angular separation of the cap 27 and housing 25. This brings the pin 112 into contact with the camming surface 115 and positions the cap 27 so that displacement of the cap 27 a second angular distance, such as thirty degrees, moves the pin along the camming surface and provides for the axial separation of the cap 27 and housing 25. It is during this second step of rotation that the O-ring 65 passes over the shoulder 105 from the engagement surface 103 to the clearance surface 101 to enhance the axial separation of the housing 25 and the cap 27.

These features, which have been described with reference to the illustrated embodiments, provide the catheter package 10 with special characteristics which enhance the process of sterilization and facilitate the controllable removal of the cap 27 from the housing 25. The disposition of the circumferential tear-strip and its line of perforations 125 relative to the plane of separation 83, offers many parameters for controlling the amount of force required to remove the cap 27. The bayonet fitting 110 and the camming surface 115 combines to provide for smooth operation of the engagement mechanism. Reliance upon the compression forces of the O-ring 65 for adding axial separation forces while the pin 112 is in contact with the camming surface 115, offers a high degree of tactile feedback to the person opening the package 10.

Although the invention has been described with reference to specific embodiments of the package 10, it will be apparent that these features, advantages and synergies can be otherwise achieved and embodied so that the scope of the invention should be ascertained only with reference to the following claims.

We claim:
1. A package, including:
   a housing;
   a cap rotatable on the housing to close the package;
   an O-ring having an outer diameter and an inner diameter, the O-ring being carried by one of the housing and the cap to form a seal between the housing and the cap;
   the other of the housing and the cap including a clearance surface having a diameter greater than the outer diameter of the O-ring, and engagement surface having a diameter less than the outer diameter of the O-ring and a shoulder disposed between the clearance surface and the engagement surface;
   the one of the housing and the cap having a groove with an axial section and a circumferential section;
   a pin extending from the other of the housing and the cap to engage the groove; and
   the O-ring being positioned to cross over the shoulder when the pin moves in the axial section of the groove.

2. The package recited in claim 1, wherein the groove is defined in part by a camming surface extending between the axial section and the circumferential section of the groove, and rotation of the gap moves the pin in the circumferential section of the groove to engage the camming surface.

3. The package recited in claim 2 wherein the pin is disposed on the housing and extends outwardly from the engagement surface.

4. The package recited in claim 2 wherein the pin is disposed on the cap and extends inwardly from the engagement surface.

5. A package for a catheter having a proximal end and a distal end, including:
 a tube defining a cavity extending between a first end and a second end of the tube along an elongate axis, the cavity being configured to receive at least the distal end of the catheter, and being sealed at the first end of the tube;
 access means disposed at the second end of the tube and being operable to provide access to the cavity of the tube;
 a housing included in the access means and having a fixed relationship with the tube, the housing communicating with the cavity in the tube;
 a cap included in the access means and being movable from a first position in proximity to the housing to a second position removed from the housing;
 means for forming a seal between the housing and the cap when the cap is in the first position;
 means for releasably locking the cap to the housing in the first position;
 portions of the cap included in the locking means and forming a groove;
 a pin included in the locking means and extending from the housing and being movable relative to the groove to releasably lock the housing member to the cap; and
 an O-ring included in the seal forming means and being disposed adjacent to the pin when the cap is in the first position.

6. The package recited in claim 5 wherein the portions of the cap define the groove with an axial section and a circumferential section.

7. The package recited in claim 6 wherein the portions of the cap define the groove with a camming surface extending between the axial section of the groove and the circumferential section of the groove.

8. A package for a catheter having a proximal end and a distal end, including:
 a tube defining a cavity extending between a first end and a second end of the tube along an elongate axis, the cavity being configured to receive at least the distal end of the catheter, and being sealed at the first end of the tube;
 access means disposed at the second end of the tube and being operable to provide access to the cavity of the tube;
 a housing included in the access means and having a fixed relationship with the tube, the housing communicating with the cavity in the tube;
 a cap included in the access means and being movable from a first position in proximity to the housing to a second position removed from the housing;
 means forming a seal between the housing and the cap when the cap is in the first position;
 means for releasably locking the cap to the housing in the first position;
 portions of the cap included in the locking means and forming a groove;
 portions of the housing included in the locking means and forming a groove;
 a pin included in the locking meams and extending from the cap, the pin being movable relative to the groove to releasably lock the housing to the cap; and
 an O-ring included in the locking means and being disposed adjacent to the pin when the cap is in the first position, 9. The package recited in claim 8 wherein the portions of the cap define the groove with an axial section and a circumferential section.

10. The package recited in claim 9 wherein the portions of the cap define the groove with a camming surface extending between the axial section of the groove and the circumferential section of the groove.

11. A method for opening a package including a housing disposed along a longitudinal axis, a cap removably fitted to the housing, and an O-ring having an outer diameter and an inner diameter forming a seal between the housing and the cap, one of the housing and the cap having a pin and the other of the housing and the cap defining a groove for receiving the pin, including the steps of:
 providing at least a portion of the groove with a camming surface;
 providing one of the housing and the cap with an O-ring clearance surface having a diameter sufficient to clear the O-ring, an O-ring engagement surface having a diameter sufficient to engage the O-ring, and a shoulder extending between the clearance surface and the engagement surface;
 rotating the cap a first angular distance to provide for an angular separation of the housing and the cap and to bring the pin into engagement with the camming surface of the groove; and
 rotating the cap a second angular distance to move the pin against the camming surface and to provide for axial separation of the cap and housing, the O-ring passing over the shoulder from the engagement surface to the clearance surface during the second rotating step to facilitate the axial separation of the cap and housing.

12. The method recited in claim 11 wherein the second providing step includes the step of providing the cap with the O-ring clearance surface.

13. The method recited in claim 11 wherein the second providing step includes the step of providing the housing with the O-ring clearance surface.

14. The method recited in claim 11 wherein the first providing step includes the step of configuring the groove with a camming surface which curves from a generally axial direction to a generally circumferential direction.

15. The method recited in claim 11 further comprising the steps of:
 providing the housing with the groove; and
 providing the cap with the pin.

16. The method recited in claim 11 further comprising the steps of:
 providing the cap with the groove; and
 providing the housing with the pin.

17. The method recited in claim 11 wherein the first providing step includes the step of:
 configuring the camming surface to extend from a generally axially direction to a generally circumferential direction.

18. The method recited in claim 11 wherein the second providing step includes the step of providing the O-ring clearance surface on the smae one of the housing and the cap as the groove.

19. The method recited in claim 11 wherein the second providing step includes the step of providing the O-ring clearance surface on the smae one of the housing and the cap as the pin.

20. The method for opening a package, comprising the steps of:
    providing the package with a housing;
    providing the package with a cap adapted to be removably fitted to the housing;
    adapting one of the housing and the cap to receive an O-ring;
    configuring the other of the housing and the cap to form a clearance surface having a diameter sufficient to clear the O-ring, an engagement surface having a diameter sufficient to engage the O-ring, and a shoulder extending between the clearance surface and the engagement surface;
    rotating the cap a first angular distance to provide for an angular separation of the housing and the cap; and
    rotating the cap a second angular distance to provide for axial separation of the cap and housing, the O-ring passing over the shoulder from the engagement surface to the clearance surface during the second rotating step to facilitate the axial separation of the cap and housing.

21. The method recited in claim 20 wherein the adapting step includes the step of providing the O-ring with an outer diameter and an inner diameter, and the configuring step includes the step of configuring the other of the housing and the cap with a clearance surface having a diameter greater than the outer diameter of the O-ring.

22. The method recited in claim 21 wherein the adapting step includes the step of providing the O-ring with an outer diameter and an inner diameter, and the configuring step includes the step of configuring the other of the housing and the cap with an engagement surface having a diameter less than the outer diameter of the O-ring.

23. The method recited in claim 20 wherein the first providing step includes the step of forming in the housing a groove defined in part by a camming surface; and
    the second providing step includes the step of forming on the cap a pin adapted to move within the groove of the housing.

24. The method recited in claim 20 wherein the first providing step includes the step of forming a pin on the housing; and
    the second providing step includes the step of forming in the cap a groove defined in part a camming surface.

25. The method recited in claim 24 wherein during the first rotating step the pin moves into contact with the camming surface of the groove.

26. The method recited in claim 24 wherein during the first rotating step the pin moved into contact with the camming surface.

* * * * *

UNITED STATES PATENT AND TRADEMARK OFFICE
CERTIFICATE OF CORRECTION

PATENT NO. : 5,217,114
DATED : June 8, 1993
INVENTOR(S) : Gadberry et al.

It is certified that error appears in the above-identified patent and that said Letters Patent is hereby corrected as shown below:

Column 3, line 24, change "hub 116" to -- hub 16 --.

Column 3, line 34, change "catheter 112" to -- catheter 12 --.

Column 4, line 19, change "package" to -- package 10.--.

Signed and Sealed this

Fifteenth Day of November, 1994

Attest:

BRUCE LEHMAN

*Attesting Officer*   *Commissioner of Patents and Trademarks*